United States Patent
Nagase et al.

(10) Patent No.: US 9,309,164 B2
(45) Date of Patent: Apr. 12, 2016

(54) METHOD FOR PURIFICATION OF SUBSTANCES CONTAMINATED WITH ORGANIC CHEMICALS

(75) Inventors: Hiroyasu Nagase, Suita (JP); Kazuhisa Miyamoto, Suita (JP); Kazumasa Hirata, Suita (JP); Hiroshi Saito, Ibaraki (JP)

(73) Assignees: OSAKA UNIVERSITY, Suita-shi (JP); ESRI CO. LTD., Ibaraki-shi (JP)

( * ) Notice: Subject to any disclaimer, the term of this patent is extended or adjusted under 35 U.S.C. 154(b) by 1177 days.

(21) Appl. No.: 12/159,497

(22) PCT Filed: Dec. 25, 2006

(86) PCT No.: PCT/JP2006/325791
§ 371 (c)(1),
(2), (4) Date: Jun. 1, 2010

(87) PCT Pub. No.: WO2007/074776
PCT Pub. Date: Jul. 5, 2007

(65) Prior Publication Data
US 2010/0234666 A1 Sep. 16, 2010

(30) Foreign Application Priority Data
Dec. 28, 2005 (JP) ................. 2005-379246

(51) Int. Cl.
*C02F 1/30* (2006.01)
*C02F 1/32* (2006.01)
(Continued)

(52) U.S. Cl.
CPC .............. *C07B 37/06* (2013.01); *A62D 3/176* (2013.01); *B09C 1/08* (2013.01); *C02F 1/32* (2013.01); *C07B 63/04* (2013.01); *C07D 319/24* (2013.01); *A62D 2101/08* (2013.01);
(Continued)

(58) Field of Classification Search
None
See application file for complete search history.

(56) References Cited

U.S. PATENT DOCUMENTS 4,414,111 A * 11/1983 Iwaisako et al. ......... 210/500.25
5,698,829 A * 12/1997 Ruddick et al. .......... 204/157.15
(Continued)

FOREIGN PATENT DOCUMENTS

EP    1 041 042    10/2000
EP    1041042    * 10/2000
(Continued)

OTHER PUBLICATIONS

Venkatadri, R et al. "Chemical Oxidation Technologies: Ultraviolet Light/Hydrogen Peroxide, Fenton's Reagent, Titanium Dioxide-Assisted Photocatalysis" Hazardous Waste and Hazardous Materials (1993).*

(Continued)

*Primary Examiner* — Melvin C Mayes
*Assistant Examiner* — Sheng H Davis
(74) *Attorney, Agent, or Firm* — Kratz, Quintos & Hanson, LLP (57) ABSTRACT

The present invention provides a method for purifying organic chemical-containing contaminated substances by which various organic chemicals (contaminants) can be readily and sufficiently decomposed in a short time, the method comprising the steps of adding a metal salt and a transition metal ionic compound to water or soil that contains organic chemicals, decomposing the organic chemicals by irradiating with light, and separating/collecting the detoxified organic chemicals.

14 Claims, 7 Drawing Sheets

(51) Int. Cl.
| | |
|---|---|
| *C07B 37/06* | (2006.01) |
| *A62D 3/176* | (2007.01) |
| *B09C 1/08* | (2006.01) |
| *C07B 63/04* | (2006.01) |
| *C07D 319/24* | (2006.01) |
| *A62D 101/08* | (2007.01) |
| *A62D 101/20* | (2007.01) |
| *A62D 101/22* | (2007.01) |
| *A62D 101/28* | (2007.01) |
| *C02F 101/30* | (2006.01) |
| *C02F 101/34* | (2006.01) |
| *C02F 101/36* | (2006.01) |

(52) U.S. Cl.
CPC ........ *A62D 2101/20* (2013.01); *A62D 2101/22* (2013.01); *A62D2101/28* (2013.01); *C02F 2101/30* (2013.01); *C02F 2101/305* (2013.01); *C02F 2101/345* (2013.01); *C02F 2101/36* (2013.01); *C02F 2305/10* (2013.01); *Y02W 10/37* (2015.05)

(56) References Cited

U.S. PATENT DOCUMENTS

| | | | |
|---|---|---|---|
| 6,242,663 B1 * | 6/2001 | Ponder et al. ............. 588/315 |
| 6,462,250 B1 * | 10/2002 | Kuriyama et al. ......... 588/306 |
| 7,442,848 B2 * | 10/2008 | Staton et al. ............. 588/401 |
| 2001/0032820 A1 | 10/2001 | Mori et al. ............... 210/763 |
| 2002/0006867 A1 * | 1/2002 | Ponder et al. ............. 502/405 |
| 2004/0084296 A1 | 5/2004 | Hori et al. ............... 204/157.15 |
| 2005/0202244 A1 * | 9/2005 | Papagianakis ............. 428/403 |
| 2005/0274663 A1 * | 12/2005 | Roitman .................. 210/252 |
| 2005/0274678 A1 * | 12/2005 | Chen et al. .............. 210/722 |
| 2006/0016689 A1 * | 1/2006 | Carson et al. ............ 205/43 |
| 2006/0138057 A1 * | 6/2006 | Machiraju et al. .......... 210/748 |
| 2006/0199215 A1 * | 9/2006 | Kinoshita et al. .......... 435/6 |
| 2007/0119779 A1 * | 5/2007 | Muramoto et al. .......... 210/639 |
| 2009/0200233 A1 * | 8/2009 | Bergendahl et al. ........ 210/636 |

FOREIGN PATENT DOCUMENTS

| | | |
|---|---|---|
| JP | 61-101232 | 5/1986 |
| JP | 61-238393 * | 10/1986 |
| JP | 5-262502 * | 10/1993 |
| JP | 7-41761 | 2/1995 |
| JP | 2000-354892 | 12/2000 |
| JP | 2003062458 * | 8/2001 |
| JP | 2003285083 * | 3/2002 |
| JP | 2002-114992 A1 | 4/2002 |
| JP | 2002-326819 A1 | 11/2002 |
| JP | 2003-93999 A1 | 4/2003 |
| JP | 2003103271 * | 4/2003 |
| JP | 2004-42011 A1 | 2/2004 |
| TW | I304085 B | 12/2008 |
| WO | WO 97/07858 | 3/1997 |
| WO | 2005/044446 A1 | 5/2005 |

OTHER PUBLICATIONS

European Search Report dated Apr. 8, 2011 (7 pages).
Keun J. Choi et al.: "Effects of activated carbon types and service life on removal of endrocrine disrupting chemicals: amitrol, nonylphenol, and bispehnol-A", *Chemosphere* 58 (2005), Elsevier, pp. 1535-1545.
N. N. Rao et al.: "Photocatalytic degradation of 2-chlorophenol: a study of kinetics, intermediates and biodegradability", *Journal of Hazardous Materials* B101 (2003), Elsevier, pp. 301-314.
Anchana Paattanasupong et al.: "Ability of a microbial consortium to remove pesticide, carbendazim and 2,4-dichlorophenoxyacetic acid", *World Journal of Microbiology & Biotechnology* 20, Kluwer Academic Publishers, 2004pp. 517-522.
International Search Report of International Application No. PCT/JP2006/325791 dated Mar. 5, 2007.
Yung-Shuen Shen, et al.; "The Effect of Light Absorbance on the Decomposition of Chlorophenols by Ultraviolet Radiation and U.V./$H_2O_2$ Processes"; *Water Research*; vol. 29; No. 3; 1995; pp. 907-914.
Young Ku, et al.; "Decompositionof 2-Chlorophenol in Aqueous Solution by UV Irradiation With the Presence of Titanium Dioxide"; *Water Research*; vol. 30; No. 11; 1996; pp. 2569-2578.
European Examination Report dated Feb. 1, 2012, in counterpart European Application No. 06843194.9.

* cited by examiner

Before UV irradiation          After UV irradiation

Dimer of bisphenol A

Trimer of bisphenol A

METHOD FOR PURIFICATION OF SUBSTANCES CONTAMINATED WITH ORGANIC CHEMICALS

TECHNICAL FIELD

The present invention relates to a method for purifying an organic chemical-containing contaminated substance conducted in the presence of at least one water-soluble alkali metal compound and/or at least one alkaline-earth metal compound, and at least one transition metal ionic compound. The present invention also relates to a system for purifying an organic chemical-containing contaminated substance.

BACKGROUND OF THE INVENTION

In recent years, environmental pollution caused by organic chemicals has become a concern in many parts of the world. In particular, many aromatic compounds possess biotoxicity, carcinogenicity, mutagenicity, endocrine disrupting activity, etc., and therefore their influence on human beings and ecosystems causes concern.

In order to prevent environmental pollution caused by organic chemicals, various laws and regulations have been enforced, but no satisfactory effect has yet been achieved. One of the probable causes of such pollution is the discharge of industrial and domestic drainage, leachate from landfills, etc., without having been satisfactorily purified. To prevent such environmental pollution, it is necessary to satisfactorily purify polluted drainage, etc., before discharging it into the surroundings.

Examples of organic chemicals that may cause environmental pollution include alkylphenols, bisphenol A, dioxin, PCBs, etc. They are difficult to decompose, exhibit endocrine disrupting activity, and adversely affect human beings and ecosystems even at low concentrations.

Examples of methods for decomposing and/or removing such organic chemicals (also referred to herein as contaminants) include biological methods utilizing microorganisms (for example, Non-patent Document 1), physical methods utilizing activated carbon and like adsorbents (for example, Non-patent Document 2), chemical methods wherein organic chemicals are decomposed by being irradiated with ultraviolet light (for example, Non-patent Document 3), etc. However, using biological methods, it is difficult to decompose a variety of contaminants with a single microorganism, and therefore a microorganism suitable for each contaminant has to be found. Moreover, even if suitable microorganisms are obtained, it is necessary to create the conditions in which the microorganisms can exhibit sufficient decomposition ability in actual practice. Furthermore, since a microorganism can decompose a contaminant only slowly, there is a problem in that the decomposition and removal of the contaminant takes time. In contrast, using physical methods, although various contaminants can be adsorbed, a separate step for treating the collected contaminants becomes necessary. Using chemical methods, organic chemicals are decomposed only at a slow rate when using a mild method and some organic chemicals cannot be decomposed at all depending on the type thereof, and therefore the use of toxic chemicals (oxidants, strong acids, etc.) is necessary to accelerate the decomposition of such organic chemicals.

In view of such circumstances, a method for decomposing and/or removing contaminants in which various contaminants can be safely and readily treated in a short time is being sought.

[Non-patent Document 1] World Journal of Microbiology & Biotechnology, 20, 517-522 (2004)

[Non-patent Document 2] Chemosphere, 58, 1535-1545 (2005)

[Non-patent Document 3] Journal of Hazardous Materials, B101, 301-314 (2003).

SUMMARY OF THE INVENTION

Problem to be Solved by the Invention

One of main objects of the present invention is to provide a simple method for purifying organic chemical-containing contaminated substances by which various organic chemicals (contaminants) can be readily and sufficiently decomposed in a short time, and a system for purifying organic chemical-containing contaminated substances.

Means for Solving the Problem

The present inventors found that, by adding a specific metal compound and a transition metal ionic compound to organic chemicals (contaminants) and subjecting the resultant mixture to light irradiation, contaminants can be effectively decomposed, and the organic chemicals become insoluble to form solid matter (insoluble matter from the decomposed organic chemicals) that can be easily removed. Methods for decomposing contaminants by irradiating light (ultraviolet light irradiation) are known; however, the facts that the decomposition speed of various contaminants remarkably improves and contaminants that cannot be decomposed by conventional techniques can be decomposed by adding specific a metal compound(s), and insolubilization of the decomposed organic chemicals can be promoted by adding a transition metal ionic compound(s) such as cobalt chloride, etc., are newly found by the present inventors. The present invention has been accomplished based on the above findings and by conducting further intensive research.

The present invention provides methods for purifying organic chemical-containing contaminated substances and a system for purifying organic chemical-containing contaminated substances as below.

Item 1. A method for purifying an organic chemical-containing contaminated substance comprising a step of irradiating the organic chemical-containing contaminated substance with light in the presence of (i) at least one water-soluble alkali metal compound and/or at least one alkaline-earth metal compound, and (ii) at least one transition metal ionic compound.

Item 2. The method according to Item 1, which comprises a first step of adding (i) at least one water-soluble alkali metal compound and/or at least one alkaline-earth metal compound, and (ii) at least one transition metal ionic compound to an organic chemical-containing contaminated substance; and a second step of irradiating a mixture obtained in the first step with light.

Item 3. The method according to Item 1, wherein said at least one water-soluble alkali metal compound and/or said at least one alkaline-earth metal compound is at least one member selected from the group consisting of calcium, magnesium, potassium, and sodium.

Item 4. The method according to Item 1, wherein at least one of the compounds (i) and (ii) is adhered to a carrier.

Item 5. The method according to Item 1, wherein a compound comprising the compound (ii) adhered to the compound (i) is used as compounds (i) and (ii).

Item 6. The method according to Item 1, wherein the compound (ii) is at least one compound of a transition metal selected from the group consisting of cobalt, manganese, iron, nickel, copper, and zinc.

Item 7. The method according to Item 1, which further comprises a third step of separating insoluble matter generated from the organic chemical after irradiating the organic chemical-containing contaminated substance with light.

Item 8. The method according to Item 1, wherein the compound (i) is dolomite.

Item 9. The method according to Item 1, wherein the organic chemical is an endocrine disruptor or an agricultural chemical.

Item 10. The method according to Item 1, wherein the organic chemical is an organochlorine compound or an aromatic compound.

Item 11. The method according to Item 1, wherein the organic chemical is a polychlorinated biphenyl (PCB) or dioxin.

Item 12. The method according to Item 1, wherein the organic chemical is at least one member selected from the group consisting of o-chlorophenol, p-chlorophenol, 2,4-dichlorophenol, p-tert-butylphenol, 1-naphthol, 3,5-xylenol, carbendazim, 17β-estradiol and bisphenol A.

Item 13. The method according to Item 1, wherein Compound (i) is added to a contaminated substance in such a manner that the concentration of Compound (i) is 0.00005-50 wt % calculated as a metallic salt unit.

Item 14. The method according to Item 1, wherein Compound (ii) is added to a contaminated substance in such a manner that the concentration of Compound (ii) is 0.01 to 10 mM.

Item 15. The method according to Item 1, wherein the light used for light irradiation is ultraviolet.

Item 16. The method according to Item 1, wherein the organic chemical-containing contaminated substance is at least one member selected from the group consisting of factory effluents, agricultural effluents, domestic drainage, sewage, leachate from waste disposal sites, exhaust gases, contaminated soil, sludge and incinerated ash.

Item 17. A method for purifying an, organic chemical-containing contaminated substance comprising the steps of:
(I) irradiating the organic chemical-containing contaminated substance with light in the presence of (i) at least one water-soluble alkali metal compound and/or at least one alkaline-earth metal compound; and then
(II) adding (ii) at least one transition metal compound.

Item 18. The method according to Item 17, which further comprises a third step of separating and collecting insoluble matter generated from the organic chemical after conducting steps (I) and (II).

Item 19. A system for purifying an organic chemical-containing contaminated substance comprising:
a photoreaction reactor for irradiating an organic chemical-containing contaminated substance with light in the presence of at least one water-soluble alkali metal compound and/or at least one alkaline-earth metal compound, and at least one transition metal ionic compound.

Item 20. The system according to Item 19, which further comprises separation and collection equipment for separating and collecting insoluble matter generated in the photoreaction reactor.

Effect of the Invention

Because a wide variety of contaminants can be treated under the same conditions, the method for purifying organic chemical-containing contaminated substances of the present invention is very useful for purifying water, soil, etc., containing various kinds of organic chemicals. In the method for purifying organic chemicals of the present invention, because the decomposition speed is very fast, organic chemicals can be treated in a short time, and therefore this method can be suitably employed to reduce the size of a purification system, to treat large amounts of waste water, etc. Furthermore, because decomposed organic chemicals can be separated and collected as insoluble matter in the method of the present invention, it can be concluded that the method of the present invention is excellent in removing organic chemicals, which are contamination sources of contaminated substances, and usable as a method for purifying contaminated substances.

The method of the present invention is different from known methods in that it does not mineralize organic chemicals, but polymerizes and insolubilizes the decomposed organic chemicals to make them easily collected, and achieves an excellent collection rate.

Furthermore, if the concentration of the organic chemicals contained in contaminated substance is low, it is difficult or impossible to purify the contaminated substance by known methods. However, the method of the invention can sufficiently purify even such a contaminated substance, and therefore it can be suitably used for purifying various contaminated substances.

Dolomite can be used in the method of the present invention as a mixture of (i) water-soluble alkali metal compounds and/or alkaline-earth metal compounds. Dolomite hitherto has been used as foodstuffs, fertilizers, etc., and its safety is confirmed. Furthermore, because dolomite can be easily obtained at low cost, the present invention can provide an inexpensive purification system.

As described above, the method for purifying organic chemical-containing contaminated substances of the present invention is very simple, safe, highly practicable, and excellent in purifying water, soil and like contaminated substances.

BEST MODE FOR CARRYING OUT THE INVENTION

1. Method for Purifying Organic Chemical-containing Contaminated Substances

The present invention encompasses the following methods.

A first method is characterized in irradiating an organic chemical-containing contaminated substance with light in the presence of (i) at least one water-soluble alkali metal compound and/or at least one alkaline-earth metal compound, and (ii) at least one transition metal ionic compound.

A second method is characterized in irradiating the organic chemical-containing contaminated substance with light in the presence of (i) at least one water-soluble alkali metal compound and/or at least one alkaline-earth metal compound; and then adding (ii) at least one transition metal compound.

The first and second methods are explained in detail below.

[First Method]

In the First method of the present invention, light irradiation is conducted under the presence of (i) at least one water-soluble alkali metal compound and/or at least one alkaline-earth metal compound, and (ii) at least one transition metal ionic compound.

The method for purifying organic chemical-containing contaminated substances of the present invention primarily comprises the following two steps:
(1) a first step of adding (i) at least one water-soluble alkali metal compound and/or at least one alkaline-earth metal compound (this may referred to as Compound (i)), and (ii) at least one transition metal ionic compound (this may referred to as Compound (ii)) to an organic chemical-containing contaminated substance, and mixing them if necessary; and (2) a second step of irradiating the mixture obtained in the first step with light.

A third step (3), wherein insolubilized organic chemicals are separated and collected, may follow the above-mentioned two steps, if necessary.

The method for purifying organic chemicals of the present invention is described in detail below.

(1) First Step

In the first step, Compound (i) and Compound (ii) are added to a contaminated substance, which is contaminated with at least one organic chemical. In this step, it is preferable to mix Compound (i) and Compound (ii) with the organic chemical-containing contaminated substance during or before irradiation of light.

(i) Water-soluble Alkali Metal Compound and/or at Least One Alkaline-earth Metal Compound Compound (i) usable in the present invention comprises an alkali metal or an alkali-earth metal and is water soluble. Specifically, Compound (i) includes hydroxides, inorganic-acid salts, organic acid salts, oxides, etc., of calcium, magnesium, potassium, and sodium.

Specific examples of Compound (i) include calcium hydroxide, magnesium hydroxide, potassium hydroxide, sodium hydroxide and like hydroxides; calcium nitrate, calcium carbonate, magnesium nitrate, magnesium carbonate, potassium nitrate, potassium carbonate, sodium nitrate, sodium carbonate and like inorganic-acid salts; calcium acetate, magnesium acetate, potassium acetate, sodium acetate, calcium citrate, magnesium citrate, potassium citrate, sodium citrate and like organic-acid salts; and calcium oxide, magnesium oxide, potassium oxide, sodium oxide and like oxides.

Among these metal compounds, calcium hydroxide, calcium oxide, calcium carbonate, magnesium hydroxide, magnesium oxide, magnesium carbonate, potassium hydroxide, and sodium hydroxide are preferable from a viewpoint of effective organic chemical decomposition.

The above-mentioned metal compounds may be used singly or in combination. Natural minerals may be used as Compound (i), and dolomite is an example of such a natural mineral.

Dolomite may also be called as magnesian limestone that is a mixture comprising calcium and magnesium as principal components. Dolomite contains calcium carbonate, magnesium carbonate, calcium oxide, magnesium oxide, calcium hydroxide, magnesium hydroxide, etc. The proportions of these constitutional components in the present invention are not limited, and any natural dolomite can be used without modification. Natural dolomite generally contains about 30 wt % calcium, and about 15 wt % magnesium, and the amount of dolomite used is suitably selected based on the contents of these metals.

It is also possible to use processed dolomite obtained by calcining, hydrating and/or aging natural dolomite. Examples of such processed dolomite include soft-burned dolomite, digested dolomite, dolomite clinker, dolomite plaster, magnesium calcium carbonate, etc.

The content of Compound (i) used in the present invention may be suitably adjusted so that the effects of the present invention may be attained, but it is preferable that Compound (i) be added in such a manner that the content of the metal compound(s) during the purification process, i.e., when Compound (i) and Compound (ii) are added to a contaminated substance, is generally about 0.00005-50 wt %, and preferably about 0.001-30 wt % calculated as a metallic compound unit. If the content of Compound (i) falls within an above range, all of Compound (i) does not have to be dissolved in water and a portion thereof may exist in a form of solid matter or particles that are insoluble in water. In the case of dolomite, it is preferable that the dolomite be mixed with organic chemicals in such a manner that the content of dolomite while irradiating with light is generally about 0.0005-10 wt %, and preferably about 0.01-1 wt %. If the content of Compound (i) or dolomite falls within an above range, wide variety of organic chemicals can be efficiently decomposed.

(ii) Transition Metal Ionic Compound

In the present invention, "transition metal ionic compounds" means metal compounds in which a transition metal becomes ions in an aqueous solution or an aqueous solution of Compound (i).

Various known transition metal ionic compounds can be used in the present invention including manganese, iron, cobalt, nickel, copper, zinc, etc. Among these, cobalt and iron are preferable. Examples of compounds of these metals include cobalt chloride, cobalt bromide, cobalt sulfate, cobalt nitrate, cobalt hydroxide, cobalt carbonate, cobalt phosphorate, cobalt acetate, cobalt ethylenediaminetetraacetate, ferric chloride, iron sulfate, iron nitrate, iron hydroxide, iron phosphorate, iron ethylenediaminetetraacetate, etc. Among these compounds, cobalt chloride, cobalt sulfate, cobalt nitrate, ferric chloride, iron sulfate, and iron nitrate are preferable.

The content of the transition metal ionic compound used in the present invention may be suitably adjusted so that the effects of the present invention can be attained, but it is preferable that the transition metal ionic compound be added in such a manner that the content of transition metal ionic compound during the purification process, i.e., when Compound (i) and Compound (ii) are added to a contaminated substance, is generally about 0.01-10 mM, and preferably about 0.1-1 mM. If the content of transition metal ionic compound falls within an above range, a variety of organic chemicals can be efficiently decomposed.

In the present invention, either or both of Compound (I) and Compound (ii) may be adhered to a carrier such as ceramics, activated carbon, etc.

Instead of using Compound (i) with Compound (ii), it is also possible to use a compound wherein Compound (ii) is adhered to Compound (i).

Organic Chemical-containing Contaminated Substance

The organic chemicals to be decomposed by the method of the present invention are organic chemicals that cause environmental pollution. Examples of such organic chemicals include endocrine disruptors, agricultural chemicals, etc. Specific examples of endocrine disruptors include polychlorinated dibenzo-p-dioxin (PCDD), polychlorinated dibenzofuran (PCDF) and like dioxins; coplanar polychlorinated biphenyl and like polychlorinated biphenyls (PCBs); organochlorine compounds such as o-chlorophenol, p-chlorophenol, 2,4-dichlorophenol and like chlorophenols; p-tert-butylphenol, 3,5-xylenol and like alkylphenols; bisphenol A, 1-naphthol and like aromatic compounds; 17β-estradiol and like natural female hormones, etc. Examples of agricultural chemicals include 2,4-dichlorophenoxyacetic acid (2,4-D), carbendazim, etc.

In particular, o-chlorophenol, 2,4-dichlorophenol, p-tert-butylphenol, 1-naphthol, 3,5-xylenol, bisphenol A, 17β-estradiol, carbendazim, etc., have extremely low decomposition rate when only conventional ultraviolet light irradiation is employed. However, by conducting light irradiation after adding Compound (i), the decomposition efficiency is significantly improved and the decomposition rate is therefore increased. Furthermore, in the method of the present invention, by adding a transition metal ionic compound as well as Compound (i), insolubilization of the decomposed organic chemicals is facilitated, and insoluble matter having a size easily filtered out is generated. In the present invention, insoluble matter means solid matter that is insoluble in water formed from insolubilized organic chemicals by being irradiated with light, and includes flotage, precipitates, etc.

There is no limitation to the form of the above-mentioned organic chemicals, and they may be contained in, for example, soils; sludge, incinerated ashes; waters such as industrial and domestic drainage, sewage, rivers, leachate from landfills (water that has seeped from soil in waste disposal sites), etc.; agricultural products and like foodstuffs; exhaust gases; waste generated in a space station, etc.

The organic chemical is mixed with Compound (i) (and a transition metal ionic compound), and, preferably, agitated to make a homogeneous mixture. Water may be added to the mixture, if necessary. The amount of water added is not limited and can be suitably selected depending on the amount and state of the contaminated substance that contains organic chemicals, and the amounts of Compound (i) (and the transition metal ionic compound).

The method of the present invention can sufficiently purify the contaminated substance in wide concentration range of the organic chemicals between about 0.1 nM and about 1 M.

It is difficult or impossible to purify a contaminated substance by known methods if the concentration of the organic chemicals contained therein is unduly low. However, the method of the present invention is also effective even if the concentration of the organic chemicals is very low.

(2) Second Step

In the second step, the mixture obtained in the first step is irradiated with light.

Light Irradiation

A mixture such as an aqueous solution, slurry, etc., obtained in the (1) first step is irradiated with light. The light used is not limited as long as it can irradiate the mixture. There is no limitation to the irradiation area, etc., but total irradiation is more advantageous as this makes the decomposition reaction progress more efficiently. In order to uniformly irradiate the mixture with light, the mixture may be agitated while irradiating with light, or the light irradiation may be conducted in a reactor, etc. The light irradiation may be conducted at room temperature or ambient temperature for about 0.1 second to about 24 hours, preferably about 1 second to about 10 hours, more preferably about 10 seconds to about 3 hours.

Ultraviolet light is the most appropriate for use in light irradiation. There is no limitation to such types of light source as long as they emit ultraviolet light. Examples of the light sources include sunlight and like natural lights; and fluorescent light, germicidal lamp, mercury lamp, deuterium lamp, xenon lamp, halogen lamp, tungsten lamp, LED and like artificial lights.

The intensity of irradiation light varies depending on the type of the light. There is no particular limit to the intensity of irradiation light; however it is generally about $0.1$ mWcm$^{-2}$ or more. The more intense the light would be the better. For example, when ultraviolet light is used, generally about $0.1$ mWcm$^{-2}$ or more, preferably about $0.1$ to about $1000000$ mWcm$^{-2}$ more preferably about $1$ to about $1000000$ mWcm$^{-2}$.

(3) Third Step

The insoluble matter generated in the second step may be separated and collected in a third step.

Separation/Collection

In the present invention, by adding an ionic transition metal, organic chemicals can be insolubilized to form insoluble matter from the detoxified organic chemicals, and therefore it is also possible to separate and collect the thus-formed insoluble matter.

Known apparatuses and methods can be used for separating/collecting such insoluble matter, and a dust collector, column, filtration apparatus, cyclone, centrifugal separator, etc., can be suitably selected depending on the status of the contaminated substance.

[Second Method]

Furthermore, the present invention also provides a purification method comprising the following steps:

(i) irradiating the organic chemical-containing contaminated substance with light in the presence of at least one water-soluble alkali metal compound and/or at least one alkaline-earth metal compound (this step may be referred to as Step (I)); and (ii) adding at least one transition metal ionic compound after conducting Step (I) (this step may be referred to as Step (II)).

The types of Compound (i) used in Step (I), types of contaminated substance, types of organic chemical, conditions for light irradiation, etc., are the same as those in the above-explained First method. The amount of Compound (i) are the same as the amount of Compound (i) added to contaminated substance as described in First method above.

The amounts and types of Compound (ii) used in Step (II) are the same as those in the above-explained First method.

In Step (II) of the second method, Compound (ii) is added to Compound (i) and an organic chemical-containing contaminated substance after irradiation. These components are mixed if necessary, and then treated at room temperature or ambient temperature for about 0.1 second to about 24 hours, preferably about 1 second to about 10 hours, more preferably about 10 seconds to about 3 hours. The mixture may be agitated or heated to accelerate the reaction, if necessary during the treatment thereby the organic chemicals is insolubilized.

Likewise the First method described above, a third step of separating/collecting the insolubilized organic chemicals may be added in the Second method after conducting step II.

Application

The first and second purification methods of the present invention can be applied to various contaminated substances such as water, incinerated ash, soil, sludge, foodstuffs, organic solvents, oils, exhaust gases, etc.

For example, in the case of purifying contaminated water, the contaminated water is stored in a reactor, reservoir, etc., and Compound (i) (and a transition metal ionic compound) is added thereto, followed by light irradiation so that the organic chemicals contained can be decomposed. In the method of the present invention, insolubilization of the organic chemicals is facilitated by adding at least one transition metal ionic compound, forming detoxified insoluble matter. By filtering (separating) this insoluble matter, organic chemicals can be removed from waste water. Neutralization of the treated waste water can be readily conducted by known methods (for example, adding acid, etc.).

Alternatively, it is possible to decompose the organic chemicals contained in the contaminated water by passing the contaminated water through a column filed with Compound (i) (and a transition metal ionic compound) to obtain an aqueous solution containing Compound (i) (and the transition metal ionic compound), and then conducting light irradiation.

One example of a method for purifying contaminated soil and/or incinerated ash is that Compound (i) (and a transition metal ionic compound), and water if necessary, are added to the soil, etc., to form a slurry, and the thus-formed slurry is irradiated with light while being agitated in a reactor. In this case, the decomposed organic chemicals are detoxified and insolubilized, forming solid matter (insoluble matter). Therefore, insoluble matter of the decomposed organic chemicals remains in the post-treated soil but separation is unnecessary.

In the case of purifying exhaust gases, a solution containing Compound (i) and a transition metal ionic compound can be sprayed into the space containing exhaust gas in the presence of water vapor, and light irradiation is then conducted. It is also possible to purify exhaust gases by spraying small particles containing Compound (i) and a transition metal ionic compound into the space containing the exhausted gas, while agitating air if necessary, and then conducting light irradiation in the presence of water vapor. In this case, insoluble matter can be removed using a dust collector, etc., if necessary. Alternatively, it is possible to purify the exhausted gas by bubbling it through a solution containing Compound (i) and a transition metal ionic compound, and then conducting light irradiation. Insoluble matter is separated/collected, if necessary.

Alternatively, it is possible to contact organic chemical-containing contaminated substance with Compound (i) or (ii) by, for example, passing an exhausted gas through carriers supporting either or both Compounds (i) and (ii).

When the contaminant is a water-insoluble liquid such as oil, etc., the organic chemical-containing oil can be purified by emulsifying them with an aqueous solution containing Compound (i) and a transition metal ionic compound by using a known emulsifier, emulsification equipment, etc., conducting light irradiation, and then separating/collecting insoluble matter if necessary.

An object of applying the technique of the present invention to agricultural products and like foodstuffs is to remove or detoxify agricultural chemicals remaining on leaves of vegetables, fruits, etc. For example, in the case of vegetables grown in fields, a mixture of Compound (i) and a transition metal ionic compound is sprayed onto the vegetables. This makes it possible to decompose the organic chemicals to form insoluble particles when exposed to sunlight. In this case, insoluble matter from the organic chemicals can be removed by washing the vegetables.

By employing the technique of the present invention, the waste generated in a space station or like space facility can be handled in space, particularly by using sun light containing ultra violet light. In many cases, conditions suitable for growing microorganisms cannot be maintained in space, and therefore it is difficult to treat organic chemicals by known biological methods. In contrast, the method of the present invention can effectively decompose organic chemicals by very simple steps without using microorganisms.

The temperature for treating organic chemicals in the present invention is not limited, and it may be an ambient temperature (room temperature).

2. System for Purifying Organic Chemical-containing Contaminated Substance

The present invention also provides a system (apparatus) for purifying organic chemicals used in the above-mentioned method for decomposing organic chemicals.

The system of the present invention comprises a photoreaction reactor and, if necessary, an insoluble matter separation/collection apparatus. The photoreaction reactor is provided with a supply port(s) and an outlet(s), whereby the contaminated substance containing organic chemicals, Compound (i), and a transition metal ionic compound are supplied into the photoreaction reactor through the supply port(s), and they axe exhausted from the outlet(s) after being treated. The supply port(s) and the outlet(s) may be provided separately or one opening may serve both functions.

There is no limitation on the form of the photoreaction reactor and it may be a bath, tank, etc. It is also possible to use a tube (pipe) as the photoreaction reactor that can mix a contaminated substance containing organic chemicals, Compound (i), a transition metal ionic compound, and water, if necessary, and flow the mixture from the supply port(s) to the outlet(s). Lakes or lagoons may also be used.

The photoreaction reactor is provided with a mixer for obtaining a mixture of organic chemicals and Compound (i) and a transition metal ionic compound, and a light irradiator for irradiating the mixture with light. There is no limitation to the mixer and a conventionally known mixing means, such as a stirrer, can be employed. There is no limitation to the light irradiator as long as it can conduct light irradiation under the conditions as described above. Examples of usable light irradiators include fluorescent lights, germicidal lamps, mercury lamps, deuterium lamps, xenon lamps, halogen lamps, tungsten lamps, LEDs, etc., but are not limited those. Natural light such as sun light may also be used as light irradiators. As described above, (ii) a transition metal ionic compound may be supplied to a photoreaction reactor together with Compound (i) and an organic chemical-containing contaminated substance, or supplied to the mixture of Compound (i) and an organic chemical-containing contaminated substance after irradiation of light. In the photoreaction reactor, organic chemicals are detoxified by being irradiated with light, and insolubilized by the transition metal ionic compound, forming solid matter.

The system of the present invention may comprise an apparatus for separating/collecting insoluble matter, if necessary, to separate/collect insoluble matter generated in the photoreaction reactor. The separation/collection apparatus is connected to the photoreaction reactor in such a manner that the mixture irradiated with light in the photoreaction reactor is transferred from the outlet of the photoreaction reactor to the separation/collection apparatus. Insoluble matter generated in the mixture in the photoreaction reactor is separated/collected by the separation/collection apparatus. The thus-obtained processed substance does not contain organic chemicals and is therefore purified.

Figure 1:
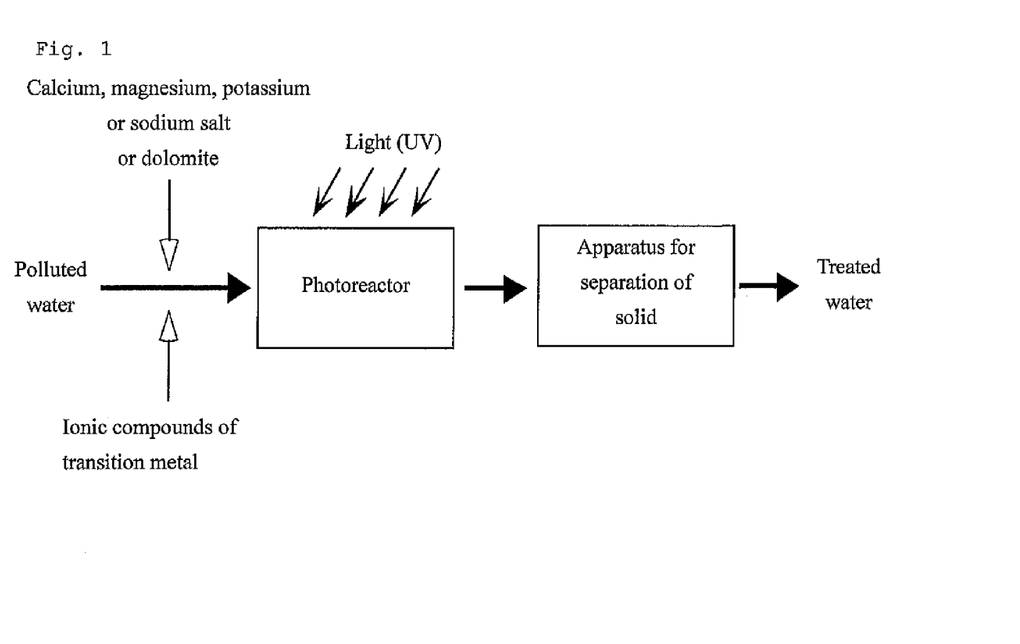
FIG. 1 is a diagram showing a treatment system of the present invention.

Examples of usable separation/collection apparatuses include dust collectors, filtration apparatuses, columns, cyclone separators, centrifugal separators, etc., but are not limited to those. The construction of the system of the present invention is shown in FIG. 1.

EXAMPLES

The present invention is explained in detail by showing Examples. However, the present invention is not limited to Examples below.

Example 1

Decomposition and Separation/Collection of 2,4-Dichlorophenol 2,4-dichlorophenol was added to 20 ml of purified water placed in a 100 ml beaker in such a manner that the concentration of the 2,4-dichlorophenol became 1 mM. Subsequently, calcium hydroxide and cobalt chloride were added to the mixture in such a manner that the concentration of calcium hydroxide became 2 mM and that of cobalt chloride became 1 mM followed by stirring sufficiently. A 15 W germicidal lamp (GL-15, product of Matsushita Electric Industrial Co., Ltd.) was placed 14 cm away from the water surface of the beaker, and the aqueous solution containing 2,4-dichlorophenol was irradiated with ultraviolet light while stirring using a stirrer. Samples were collected before and after irradiation of ultraviolet light. The samples subjected to 60 minutes irradiation became brown suspensions. These suspensions were subjected to filtration using two types of filter papers No. 2 and No. 5C (product of Advantec), and the optical densities of the thus-obtained filtrates at 400 nm were measured using an absorptiometer U-2000 (product of Hitachi). The concentration of 2,4-dichorolophenol in the filtrate was measured by using a high-performance liquid chromatography (product of Hitachi).

Figure 2:
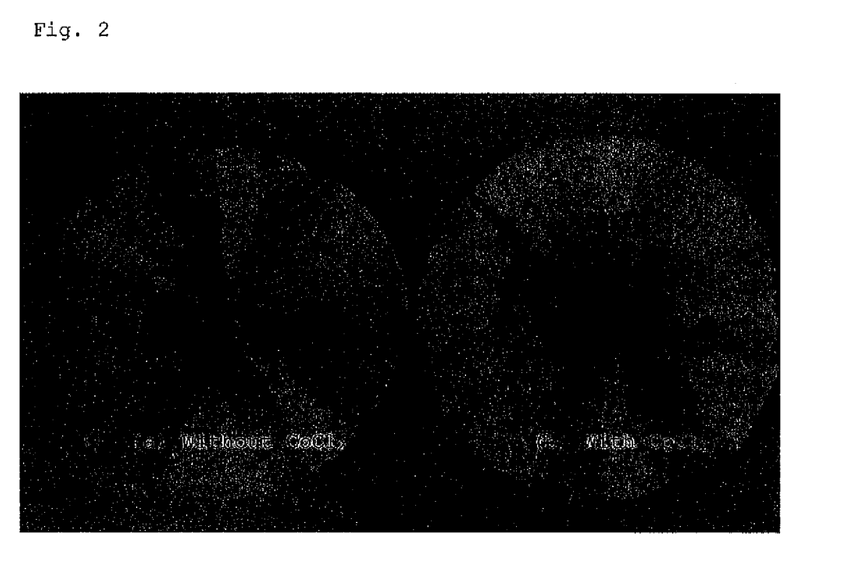
FIG. 2 is a photograph of filtered insoluble matter generated by decomposition of 2,4-dichlorophenol.
Figure 3:
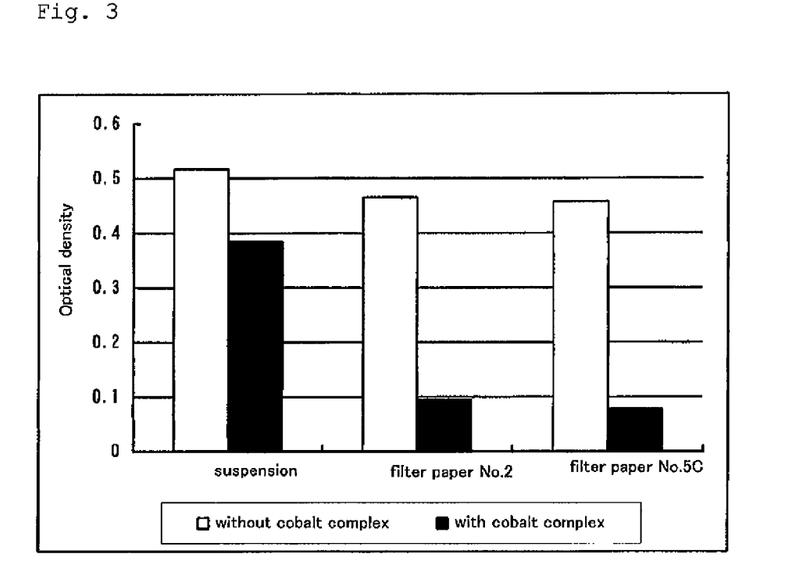
FIG. 3 is a graph showing that insolubilization of decomposed organic chemical is accelerated by addition of cobalt chloride.

As a result, 90% or more of 2,4-dichrolophenol was reduced. As shown in FIG. 2, solid matter (insoluble matter from the decomposed organic chemicals) were separated/collected on the filter papers by adding cobalt chloride. Optical densities of the filtrates were measured, revealing that those filtrates to which cobalt chloride was not added had an optical density almost the same as that of the suspension, but that filtrate to which cobalt chloride ($CoCl_2$) was added had optical densities about $1/4^{th}$ that of the suspension respectively (see FIG. 3). From the fact that the filter papers No. 2 and No. 5C have particle holding sizes (minimum particle diameter of the particles retained by the filter paper and which do not flow into the filtrate) were about 5 μm and about 1 μm respectively, it became clear that solid matter larger than 5 μm is formed by adding cobalt chloride and such solid matter can be removed by filtration.

Instead of using a filter paper, the brown suspensions could be passed through a glass column (diameter: 5 cm, length: 10 cm) filled with 30-50 mesh sea sand (product of Nacalai Tesque, Inc.) to the height of 5 cm. As a result, solid matter in the suspensions was completely separated/collected, giving transparent filtrates.

Example 2

Decomposition of Various Organic Chemicals

Bisphenol A was added to 50 ml of purified water placed in a 100 ml beaker in such a manner that the concentration of the bisphenol A became 100 μM. Subsequently, 0.20 g of dolomite was added to the mixture and stirred. A 15 W germicidal lamp (GL-15, product of Matsushita Electric Industrial Co., Ltd.) was placed cm away from the water surface of the beaker, and the resultant aqueous solution was irradiated with ultraviolet light while stirring using a stirrer. Samples were collected before and after irradiation of ultraviolet light.
(a) Measurement of a Decomposition Rate The collected samples were subjected to centrifugal separation (10000 rmp, 5 minutes) to collect the supernatants. To 135 μl of supernatant was added 15 μl of HCl (6 N). The concentration of bisphenol A was measured using high performance liquid chromatography (HPLC). The extent of decomposition was determined from measurement at 280 nm using a reversed phase column (5C18-AR-II, product of Nacalai Tesque, Inc.) through which methanol/water=50/50 (v/v) was eluted as the mobile phase at 1 ml/min, and 10 μl of each sample was injected.
(b) Decomposition of Various Organic Chemicals In the same manner, the extents of decomposition of tetrachlorobisphenol A; o-chlorophenol; p-chlorophenol; 2,4-dichlorophenol; p-tert-butylphenol; 2,4-dichlorophenoxy acetic acid (2,4-D); carbendazim; 17-β-estradiol; 1-naphthol and 3,5-xylenol were determined (irradiation with UV, dolomite added). For comparison, the extents of decomposition of the same organic chemicals were determined without adding dolomite (only irradiation of ultraviolet light). The extent of decomposition is expressed as the percentage reduction after 60 minutes of reaction from the initial concentration of each organic chemical.

Table 1 shows the results. As shown in Table 1, various endocrine disruptor compounds were decomposed satisfactory. Furthermore, from the fact that decomposition of 2,4-dichlorophenol and tetrachlorobisphenol A both having a plurality of chlorine substituents were also accelerated, it can be concluded that decomposition of various other photodegradable chlorinated compounds with a plurality of chlorine substituents, such as dioxins and PCBs, can also be accelerated.

TABLE 1

| Organic Chemicals | Initital concentration (μM) | 60 minutes of decomposition | |
|---|---|---|---|
| | | UV + Dolomite | UV only |
| Bisphenol A | 100 | 70 | 0 |
| Tetrachrolobisphenol A | 50 | 100 | 31 |
| o-Chlorophenol | 100 | 100 | 28 |
| p-Chlorophenol | 100 | 100 | 52 |
| 2,4-Dichlorophenol | 100 | 100 | 0 |
| p-tert-Butylphenol | 100 | 94 | 18 |
| 2,4-D | 100 | 13 | 6 |
| Carbendazim | 40 | 88 | 8 |
| 17-β-Estradiol | 10 | 100 | 0 |
| 1-Naphthol | 100 | 94 | 32 |
| 3,5-Xylenol | 100 | 51 | 7 |

Example 3

Decomposition Using Various Compound (i)

To 50 ml of pure water placed in a 100 ml beaker was added bisphenol A (BPA) to a concentration of 100 μM. Subsequently, 44 mg of calcium oxide, 58 mg of calcium hydroxide, 25 mg of magnesium oxide, 36 mg of magnesium hydroxide, 52 mg of magnesium carbonate or 63 mg of sodium hydroxide was added to a beaker. A 15 W germicidal lamp (GL-15, product of Matsushita Electric Industrial Co., Ltd.) was placed 12 cm away from the water surface of the beaker, and the resultant aqueous solution was irradiated with ultraviolet light while stirring using a stirrer. Samples were collected every 20 minutes.

Figure 4:
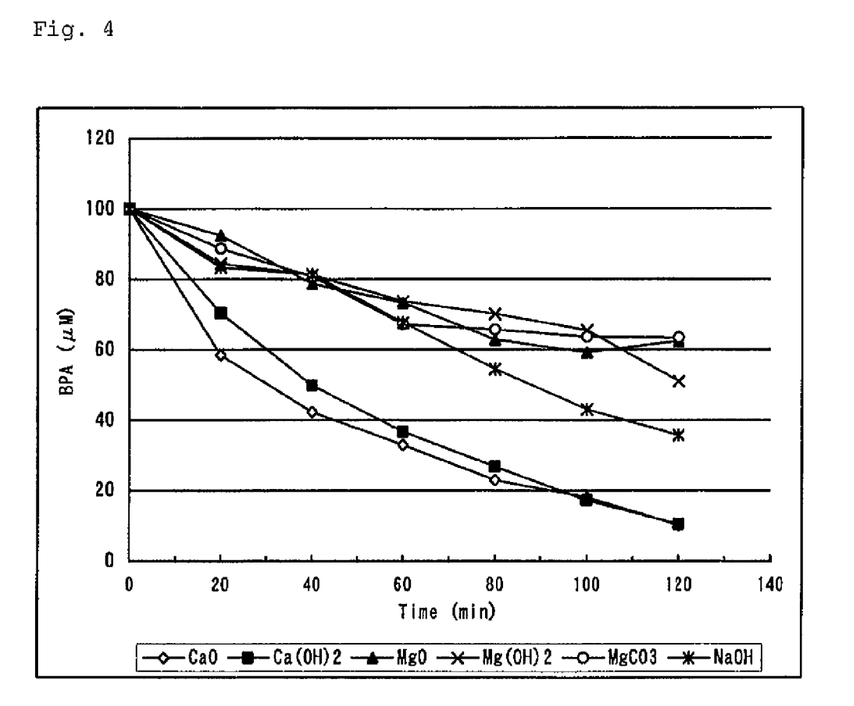
FIG. 4 is a graph showing that bisphenol A can be decomposed by addition of various metal compounds (i).

As a result, as shown in FIG. 4, it became clear that bisphenol A can be decomposed by using alkali metal compounds and/or alkaline-earth metal compounds.

Example 4

Decomposition and Separation/Collection Using Various Compound (i)

Cobalt chloride was added to 20 ml of 1 mM 2,4-dichlorophenol in the same manner as in Example 1 in such a manner that the concentration of the cobalt chloride became 1 mM. Instead of calcium hydroxide, one member selected from calcium oxide, calcium carbonate, magnesium hydroxide, magnesium oxide, magnesium carbonate, potassium hydroxide, and sodium hydroxide was added to the resultant mixture in such a manner that its concentration became 2 mM. Alternatively, 4 mg of dolomite may be added to the mixture. The mixtures were irradiated with ultraviolet light for 60 minutes, and then subjected to filtration using two types of filter papers No. 2 and No. 5C. Optical densities of the thus-obtained filtrates at 400 nm were measured.

Figure 5:
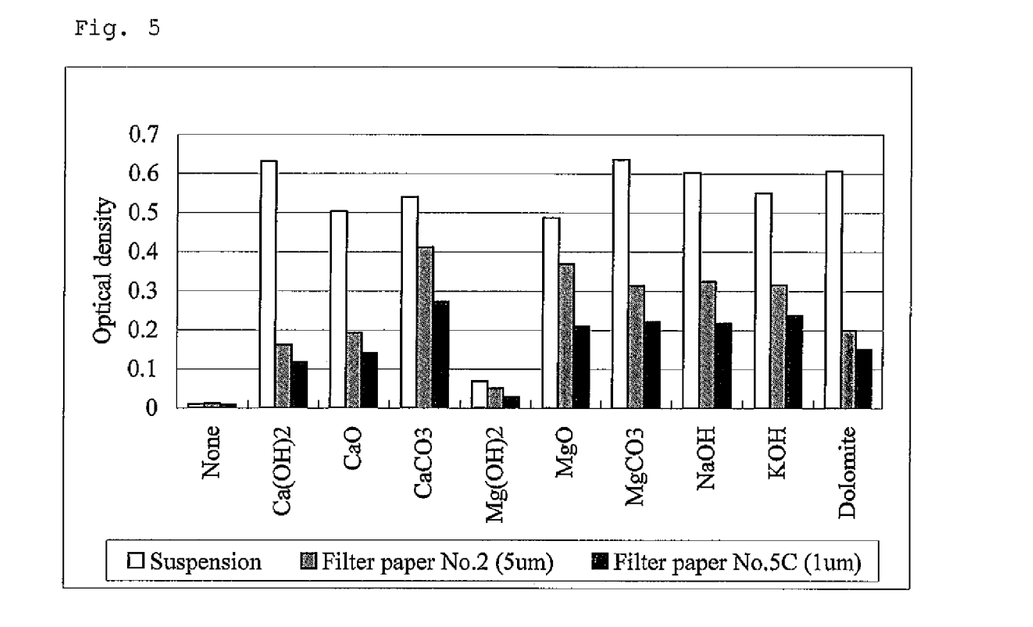
FIG. 5 is a graph showing that insolubilization of 2,4-dichlorophenol is accelerated by addition of various metal compounds (i).

As a result, all samples to which a metallic compound of calcium, magnesium, potassium or sodium, or dolomite was added became brown suspensions. Optical densities of the filtrates obtained by subjecting the resultant suspensions to filtration were measured, revealing that, as shown in FIG. 5, formation of solid matter was also facilitated when one of these metallic compounds or dolomite was added as when a calcium hydroxide ($Ca(OH)_2$) was added. Therefore, it is believed that metallic compounds of calcium, magnesium, potassium, and sodium, and various minerals containing such metallic compound(s) can achieve such effects.

Example 5

Decomposition and Separation/Collection Using Various Transition Metals

Calcium hydroxide was added to 1 mM 2,4-dichlorophenol in the same manner as in Example 1 in such a manner that the concentration of the calcium hydroxide became 2 mM. Instead of cobalt chloride, one member selected from cobalt nitrate, manganese chloride, manganese nitrate, ferric chloride, ferric nitrate, nickel chloride, nickel nitrate, copper chloride, copper nitrate, zinc chloride, zinc nitrate, titanium oxide, and ferric oxide was added to the resultant mixture so that its concentration became 1 mM. The resultant mixtures were subjected to 60 minutes irradiation and the resultant suspensions were then filtered using two types of filter papers No. 2 and No. 5C. The optical densities of the thus-obtained filtrates at 400 nm were measured using.

Figure 6:
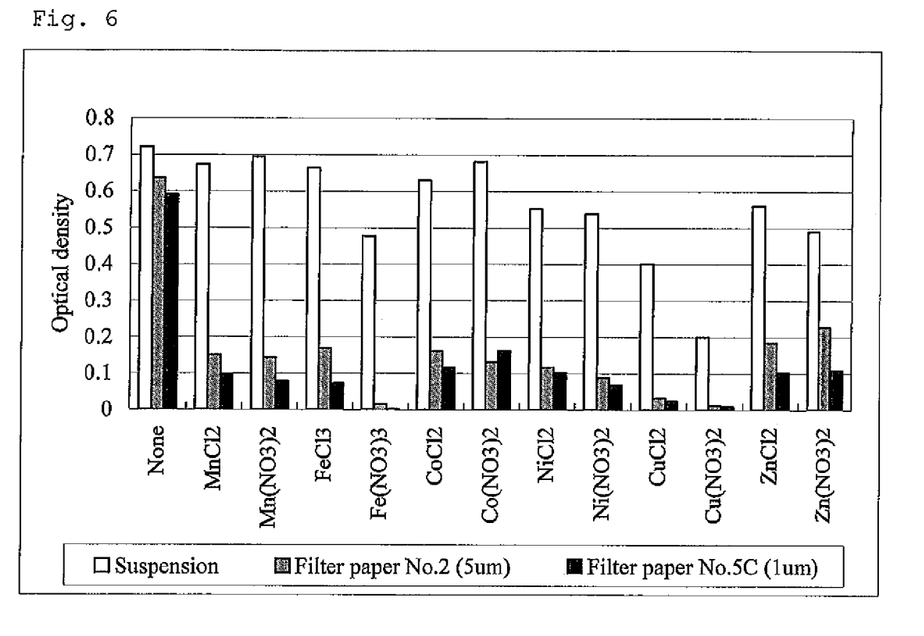
FIG. 6 is a graph showing that insolubilization of 2,4-dichlorophenol is accelerated by addition of various transition metal salts.

As a result, all samples to which a chloride salt or a nitrate salt of transition metal was added became brown suspensions. Optical densities of the filtrates obtained by subjecting the resultant suspensions to filtration were measured. As shown in FIG. 6, in all samples to which a chloride salt or a nitrate salt of transition metal was added, the optical densities of the filtrates obtained by using filter papers No. 2 and No. 5C were significantly reduced compared to that of the suspension. However, when the same experiments were conducted using a titanium oxide and an ferric oxide, which are often used as photocatalysts and/or oxidation catalysts, any facilitatory effects for forming solid matter were not observed. Titanium oxides and ferric oxides do not achieve such effect presumably because they are insoluble in water. The effects of addition of a chloride salt or a nitrate salt are described in this example; however, it can be easily concluded that formation of solid matter can be facilitated by adding any transition metal compounds that form ions when dissolved in water.

Example 6

Decomposition and Separation/Collection of Various Organic Chemicals

In the same manner as in Example 1, bisphenol A instead of 2,4-dichlorophenol was added so as to have a concentration of 0.5 mM. Subsequently, calcium hydroxide and cobalt chloride were added to have a concentration of 2 mm and 1 mM respectively. After conducting 60 minutes ultraviolet light irradiation, the resultant suspensions were subjected to filtration using two types of filter papers No. 2 and No. 5C, and the optical densities of the thus obtained filtrates at 400 nm were measured.

In the same manner, each of o-chlorophenol; p-chlorophenol; p-tert-butyl phenol; 1-naphthol; 3,5-xylenol; and 2,4-dichlorophenoxy acetic acid (2,4-D) were added so as to have a concentration of 1 mM. After irradiation of ultraviolet light, the optical densities of the resultant suspensions were measured.

Figure 7:
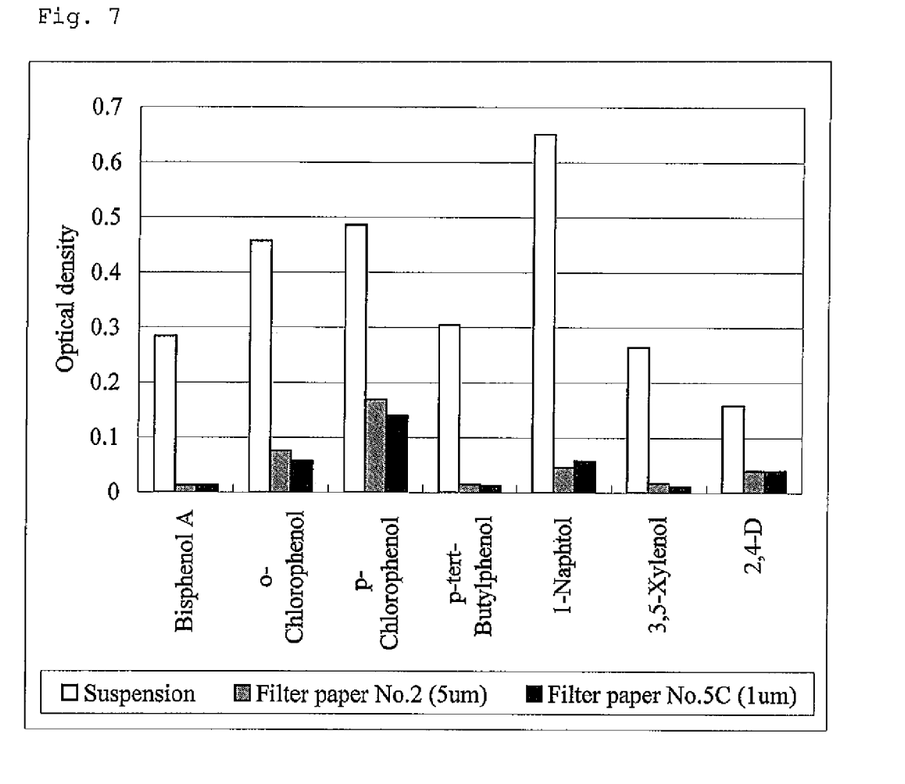
FIG. 7 is a graph showing that insolubilization of various organic chemicals can be accelerated.

FIG. 7 shows the results. These organic chemicals were satisfactory decomposed and solid matter was formed. Therefore, it became clear that this method is applicable to decompose organic chemicals. Furthermore, because all these organic chemicals are endocrine disruptors, it can be concluded that this method is also effective for decomposing aromatic compounds comprising other endocrine disruptors having a similar construction. Furthermore, considering the fact that decomposition of chlorophenols having at least one chloro-substituent, decomposition of 2,4-D, and formation of solid matter can be facilitated, this method is also applicable to treat various photodegradable organic chemicals having chloro-substituent.

Example 7

Treatment of Solid Contaminated-substance Containing Organic Chemicals

An example of evaluation of treatment of solid contaminated-substance containing organic chemicals, such as contaminated soil, sludge, and incinerated ash, was explained below. To 20 g of sea sand (30-50 mesh, product of Nacalai Tesque, Inc.) was added 10 ml of 1 mM 2,4-dichlorophenol solution, followed by sufficient stirring. Water (10 ml) containing 4 mM calcium hydroxide and 2 mM cobalt chloride was added to the resultant mixture to give slurry, and the obtained slurry was placed in a cylindrical quartz tube. The slurry was irradiated with ultraviolet light for 60 minutes using a germicidal lamp placed 10 cm away therefrom while agitating by rotation. After the reaction, the slurry was subjected to 2,4-dichlorophenol extraction using methanol, and the 2,4-dichlorophenol concentration was then measured using a high-performance liquid chromatography.

Figure 8:
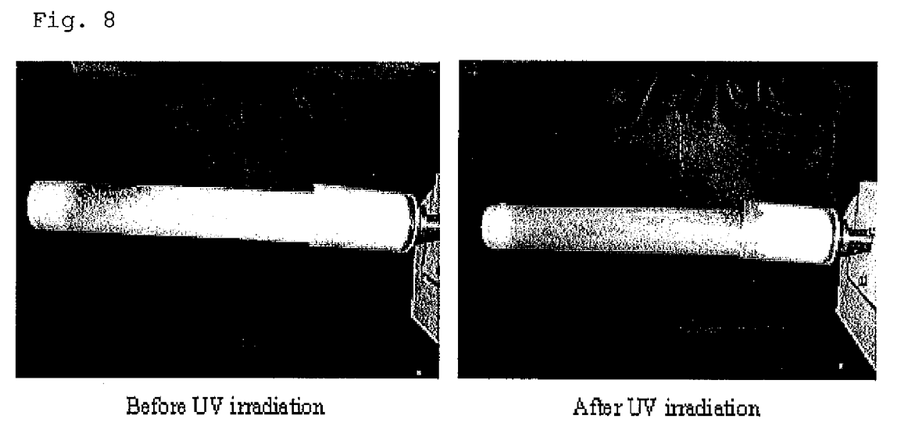
FIG. 8 is a picture showing that a solid contaminated substance containing organic chemicals can be treated.

After 60 minutes irradiation of ultraviolet light, the concentration of 2,4-dichlorophenol was reduced to $1/10^{th}$. Photographs before and after irradiation of ultraviolet light are shown in FIG. 8. The sea sand was white before ultraviolet light irradiation but it became brown after the irradiation. This indicates that insoluble solid matter was formed from 2,4-dichlorophenol. This result made it clear that solid contaminated-substance containing organic chemicals can be purified by irradiating it with ultraviolet light after forming it into slurry.

Example 8

Verification of Polymerization

In order to verify the occurrence of polymerization, a solution irradiated with ultraviolet light after adding calcium hydroxide and cobalt chloride to bisphenol A was inspected using a high-performance liquid chromatograph mass spectrometer (NanoFrontier LD, product of Hitachi).

Figure 9:
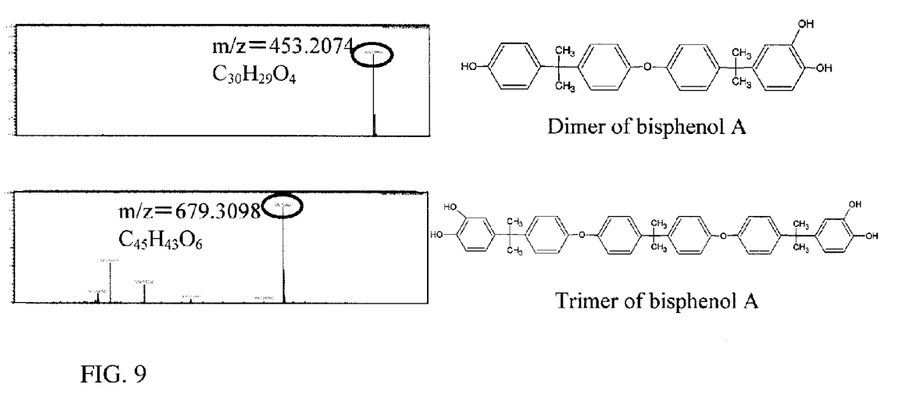
FIG. 9 shows formation of polymerization products of bisphenol A.

FIG. 9 shows the results. Peaks at mass numbers of 453 and 679, which are presumably attributable to a dimer and a trimer of bisphenol A, are observed. This confirms the occurrence of polymerization of bisphenol A. The structural formulae shown at the right of the figure are examples of the expected dimer and trimer. Peaks attributable to higher than tetramer were not observed. Presumably, this is because such substances have high molecular weights and are insoluble in solvent. From these results, it can be concluded that insoluble matter is formed in this reaction due to polymerization of organic chemicals.

Example 9

Timing for Adding Transition Metal Compound

Calcium hydroxide was added to 20 ml of 1 mM 2,4-dichlorophenol in the same manner as in Example 1 to have a concentration of 2 mM. Cobalt chloride was added to the resultant mixture to have a concentration of 1 mM, and then the solution was irradiated with ultraviolet light while stirring for 60 minutes. After irradiation of ultraviolet light, the solution was stirred for 60 minutes (this sample is referred to as Before UV). Alternatively, the mixture of calcium hydroxide and 2,4-dichlorophenol was irradiated with ultraviolet light for 60 minutes and cobalt chloride was then added thereto so that the concentration thereof became 1 mM, and then was stirred for 60 minutes (this sample is referred to as After UV). Another sample was obtained by irradiating ultraviolet light for 60 minutes without adding cobalt chloride, and then the resultant suspension was stirred for 60 minutes (this sample is referred to as Nothing). These samples were subjected to filtration using two types of filter papers No. 2 and No. 5C, and the optical densities of the thus obtained filtrates at 400 nm were measured.

Figure 10:
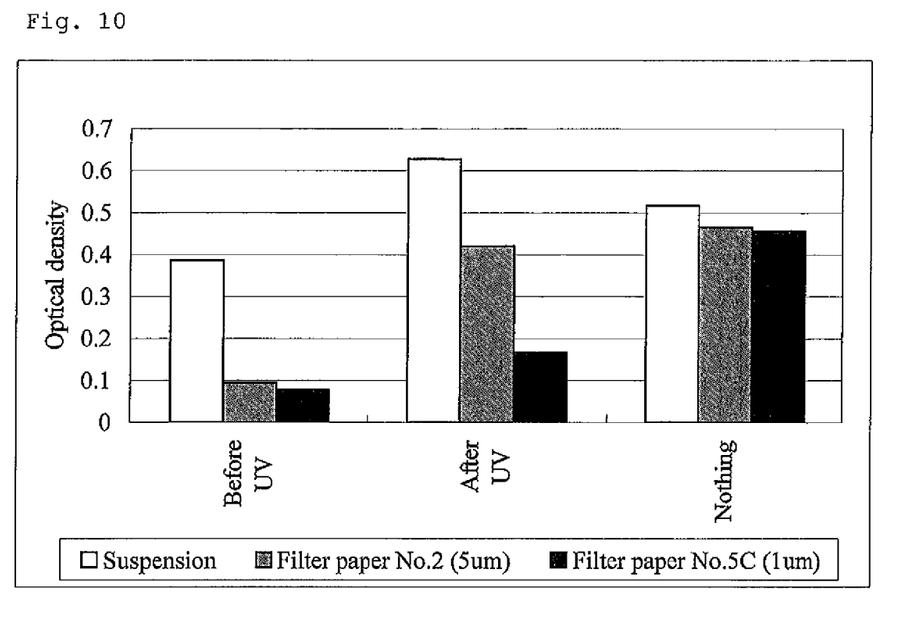
FIG. 10 is a graph showing formation of insoluble matter when a cobalt salt is added after irradiation of ultraviolet light (After UV).

The result reveals that even a case when cobalt chloride was added after irradiation of ultraviolet light (After UV), formation of insoluble matter was also facilitated (FIG. 10). Therefore, it can be concluded that the preferable timing for adding a transition metal compound is before irradiation of ultraviolet light but it is still effective even after irradiation of ultraviolet light.

Example 10

Treatment of Dioxin and PCB

In the same manner as in Example 1, to 50 ml of purified water placed in a 100 ml beaker, a PCB mixture (KC-400, product of Kaneka Corporation) was added so as to have a concentration of 0.02 mg/L, or 2,3-dichlorodibenzo-p-dioxin (product of Supelco, Inc.) was added so as to have a concentration of 0.01 mg/L instead of 2,4-dichlorophenol. Subsequently, calcium hydroxide and cobalt chloride were added to have a concentration of 2 mM and 1 mM respectively. A 15 W germicidal lamp was placed 12 cm away from the water surface of the glass beaker, and the resultant aqueous solution was irradiated with ultraviolet light while stirring using a stirrer for 20 minutes. After ultraviolet light irradiation, samples were collected and concentrated by solid phase extraction. Concentrations of dioxin and PCB were measured with a gas chromatograph mass spectrometer (GC-MS).

With regard to the samples subjected to only ultraviolet light irradiation, the extent of removal of PCBs having 1 to 5 chlorines was 34-64%, and that of 2,3-dichlorodibenzo-p-dioxin was about 87%. In contrast, by irradiating the samples with ultraviolet light after adding calcium hydroxide and cobalt chloride, the extents of removal of the PCBs and dioxin were increased to 98-100%.

The invention claimed is:

1. A method for purifying an aromatic compound-containing contaminated substance comprising:
a first step of irradiating the aromatic compound-containing contaminated substance with light in the presence of (i) at least one water-soluble alkali metal compound and/or at least one water-soluble alkaline-earth metal compound selected from the group consisting of calcium compounds, magnesium compounds, potassium compound, and sodium compounds, and (ii) at least one transition metal ionic compound selected from the group consisting of cobalt compounds, manganese compounds, nickel compounds, copper compounds and zinc compounds, whereby the aromatic compound is polymerized,
wherein the transition metal ionic compound is a metal compound in which a transition metal becomes ions in an aqueous solution; and
a second step of collecting the polymerized aromatic compound that is generated in the first step.

2. The method according to claim 1, wherein the first step comprises the steps of:
(1) step of adding the compound (i) at least one water-soluble alkali metal compound and/or at least one alkaline-earth metal compound, and the compound (ii); and
(2) a step of irradiating a mixture obtained in the first step with light.

3. The method according to claim 1, wherein at least one of the compounds (i) and (ii) is adhered to a carrier.

4. The method according to claim 1, wherein a compound comprising the compound (ii) adhered to the compound (i) is used as compounds (i) and (ii).

5. The method according to claim 1, wherein the method further comprises a step of separating the polymerized aromatic compound between the first step and the second step.

6. The method according to claim 1, wherein the compound (i) is dolomite.

7. The method according to claim 1, wherein the aromatic compound is a polychlorinated biphenyl (PCB) or dioxin.

8. The method according to claim 1, wherein the aromatic compound is at least one member selected from the group consisting of o-chlorophenol, p-chlorophenol, 2,4-dichlorophenol, p-tert-butylphenol, 1-naphthol, 3,5-xylenol, carbendazim, 17β-estradiol and bisphenol A.

9. The method according to claim 1, wherein the light used for light irradiation is ultraviolet.

10. The method according to claim 1, wherein the aromatic compound-containing contaminated substance is at least one member selected from the group consisting of factory effluents, agricultural effluents, domestic drainage, sewage, leachate from waste disposal sites, exhaust gases, contaminated soil, sludge and incinerated ash.

11. The method according to claim 1, wherein the transition metal ionic compound is at least one compound selected from the group consisting of cobalt chloride, cobalt bromide, cobalt sulfate, cobalt nitrate, cobalt hydroxide, cobalt carbonate, cobalt phosphorate, cobalt acetate, cobalt ethylenediaminetetraacetate, manganese chloride, manganese nitrate, nickel chloride, nickel nitrate, copper chloride, copper nitrate, zinc chloride and zinc nitrate.

12. The method according to claim 1, wherein said at least one water-soluble alkali metal compound and/or said at least one alkaline-earth metal compound is at least one member selected from the group consisting of water-soluble compounds of hydroxides, inorganic-acid salts, organic acid salts and oxides of calcium, magnesium, potassium and sodium.

13. A method for purifying an aromatic compound-containing contaminated substance wherein the method comprises the steps of:
(I) irradiating the aromatic compound-containing contaminated substance with light in the presence of (i) at least one water-soluble alkali metal compound and/or at least one water-soluble alkaline-earth metal compound selected from the group consisting of calcium compounds, magnesium compounds, potassium compound, and sodium compounds; and then
(II) adding (ii) at least one transition metal ionic compound selected from the group consisting of cobalt compounds, manganese compounds, nickel compounds, copper compounds and zinc compounds, whereby the aromatic compound is polymerized,
wherein the transition metal ionic compound is a metal compound in which a transition metal becomes ions in an aqueous solution; and
(III) collecting the polymerized aromatic compound that is generated in step (II).

14. The method according to claim 13, wherein the method further comprises separating the polymerized aromatic compound between step (II) and step (III).

* * * * *